United States Patent [19]

Deutsch et al.

[11] Patent Number: 5,595,724
[45] Date of Patent: Jan. 21, 1997

[54] TREATED CALCIUM/OXYANION-CONTAINING PARTICLES FOR MEDICAL DIAGNOSTIC IMAGING

[76] Inventors: Edward A. Deutsch; Karen F. Deutsch, both of 12805 Maryland Estates Ct., Maryland Heights, Mo. 63043; Dennis L. Nosco, 1026 Driftwood Trails Dr., Florissant, Mo. 63031; William H. Ralston, 22 Rathsallagh Ct., St. Charles, Mo. 63304; David H. White, 877 Gardenway Dr., Ballwin, Mo. 63011; Janet B. Wilking, 819 Moundale Dr., Ferguson, Mo. 63135; Robert G. Wolfangel, 1104 Grenadier La., Ballwin, Mo. 63021; Steven R. Woulfe, 1719 Woodmore Oaks Dr., Ballwin, Mo. 63021; William P. Cacheris, 16726 Edisto Ct., Florissant, Mo. 63034; Linda Meeh, 6028 Odell, St. Louis, Mo. 63139

[21] Appl. No.: 373,152

[22] Filed: Jan. 13, 1995

Related U.S. Application Data

[60] Division of Ser. No. 47,129, Apr. 13, 1993, Pat. No. 5,407,659, which is a continuation-in-part of Ser. No. 948,540, Sep. 22, 1992, Pat. No. 5,344,640, which is a continuation-in-part of Ser. No. 784,325, Oct. 22, 1991, abandoned.

[51] Int. Cl.$^6$ ........................................... A61B 8/00
[52] U.S. Cl. ................. 424/9.5; 436/173; 128/662.02; 423/263; 423/301; 423/305; 556/19; 534/15; 424/602
[58] Field of Search ............ 424/9.5, 602; 436/173; 128/662.02; 423/263, 301, 305; 556/19; 534/15

[56] References Cited

U.S. PATENT DOCUMENTS

| | | | |
|---|---|---|---|
| 4,079,124 | 3/1978 | Winchell | 424/4 |
| 4,243,652 | 1/1981 | Francis | 424/1 |
| 4,657,755 | 4/1987 | Christensen et al. | 424/1.1 |
| 4,680,171 | 7/1987 | Shell | 424/5 |
| 4,709,703 | 12/1987 | Lazarow et al. | 128/654 |
| 4,853,225 | 8/1989 | Wahlig et al. | 424/423 |
| 4,880,007 | 11/1989 | Sadler et al. | 128/653 |
| 4,888,248 | 12/1989 | Hirai et al. | 438/403 |
| 5,047,031 | 9/1991 | Constantz | 606/77 |
| 5,055,307 | 10/1991 | Tsuru et al. | 424/493 |
| 5,122,363 | 6/1992 | Balkus, Jr. et al. | 424/9 |
| 5,186,922 | 2/1993 | Shell et al. | 128/654 |
| 5,330,742 | 7/1994 | Deutsch et al. | 424/9 |
| 5,342,609 | 8/1994 | Meeh et al. | 424/9 |
| 5,407,659 | 4/1995 | Deutsch et al. | 424/9 |

FOREIGN PATENT DOCUMENTS

| | | | |
|---|---|---|---|
| 0393399 | 11/1983 | European Pat. Off. | C09K 11/463 |
| 0343934 | 11/1989 | European Pat. Off. | H01F 1/36 |
| 0361797 | 4/1990 | European Pat. Off. | C03C 10/00 |
| 85/02772 | 7/1985 | WIPO | A61K 49/00 |

OTHER PUBLICATIONS

Mayer et al., J. Inorg. Biochem. 45(2):129–133 (1992).
Okazaki, M., Biomaterials 12:46–49 (1991).

*Primary Examiner*—Gary E. Hollinden
*Attorney, Agent, or Firm*—Brian K. Stierwalt

[57] ABSTRACT

Treated calcium/oxyanion-containing particles are disclosed for enhancing medical diagnostic imaging such as magnetic resonance imaging ("MRI"), magnetic resonance spectroscopy ("MRS"), magnetic resonance spectroscopy imaging ("MRSI"), X-ray diagnostic imaging, and ultrasound imaging. Novel coating and manufacturing techniques are disclosed to control particle size and particle aggregation resulting in compositions for organ specific imaging of the liver, spleen, or tissue disease states is obtained. Depending on the diagnostic imaging technique, calcium/oxyanion-containing particles are treated to be paramagnetic, radiopaque, or echogenic. Also disclosed are diagnostic compositions and methods of performing medical diagnostic procedures which involve administering to a warm-blooded animal a diagnostically effective amount of the above-described particles and then performing the medical diagnostic procedure.

21 Claims, No Drawings

TREATED CALCIUM/OXYANION-CONTAINING PARTICLES FOR MEDICAL DIAGNOSTIC IMAGING

CROSS REFERENCE TO RELATED APPLICATIONS

This is a division of application Ser. No. 08/047,129 filed on Apr. 13, 1993, U.S. Pat. No. 5,407,659, which is a continuation-in-part of U.S. patent application Ser. No. 07/948,540, filed Sep. 22, 1992, U.S. Pat. No. 5,344,640, titled "Treated Apatite Particles for Medical Diagnostic Imaging," which is continuation-in-part of U.S. patent application Ser. No. 07/784,325, filed Oct. 22, 1991, abandoned, titled "Treated Apatite Particles for Medical Diagnostic Imaging," which applications are incorporated herein by reference.

BACKGROUND OF THE INVENTION

This invention relates to treated calcium/oxyanion-containing particles and their use in medical diagnostic imaging techniques, such as magnetic resonance imaging ("MRI"), magnetic resonance spectroscopy ("MRS"), magnetic resonance spectroscopy imaging ("MRSI"), X-ray, and ultrasound. The present invention also includes novel apatite and apatite precursor particles, manufacturing methods, and coating compositions which prevent particle aggregation, improve particle stability, and permit functionalization of the particle surface.

The use of contrast agents in diagnostic medicine is rapidly growing. In X-ray diagnostics, for example, increased contrast of internal organs, such as the kidneys, the urinary tract, the digestive tract, the vascular system of the heart (angiography), etc., is obtained by administering a contrast agent which is substantially radiopaque. In conventional proton MRI diagnostics, increased contrast of internal organs and tissues may be obtained by administering compositions containing paramagnetic metal species which increase the relaxivity of surrounding protons. In ultrasound diagnostics, improved contrast is obtained by administering compositions having acoustic impedances different than that of blood and other tissues.

Often it is desirable to image a specific organ or tissue. Effective organ- or tissue-specific contrast agents accumulate in the organ or tissue of interest.

From the foregoing, it would be an important advancement in the art to provide organ specific medical diagnostic imaging agents. Specifically, it would be an improvement in the art to provide organ specific MRI, X-ray, and ultrasound contrast agents.

Such medical diagnostic imaging agents are disclosed and claimed herein.

SUMMARY OF THE INVENTION

The present invention provides methods and compositions for improved medical diagnostic imaging. The imaging agents are derived from calcium/oxyanion-containing particles including, but not limited to, apatites, apatite precursors, hydroxyapatite (sometimes referred to as "hydroxylapatite"), fluoroapatite, iodoapatite, carbonateapatite, and mixtures and derivatives thereof.

By controlling the particle size and route of administration, organ specific imaging of the liver, spleen, gastrointestinal tract, or blood pool is obtained. Typical particle sizes are in the range from about 10 nm to about 50 μm depending upon the organ or disease state to be imaged, the mechanism of delivery of the particles to the organ or disease state, and the medical diagnostic imaging technique utilized. In addition, calcium/oxyanion particles within the range from 1 nm to about 50 nm may also be used to image the blood pool.

Depending on the diagnostic imaging technique, calcium/oxyanion-containing particles are treated to be paramagnetic, radiopaque, or echogenic. For example, paramagnetic species may be incorporated into the particles to improve magnetic resonance contrast, and radiopaque species may be incorporated into the particles to provide X-ray contrast. Particle density, and corresponding echogenic characteristics, can be controlled to impart low or high acoustic impedance relative to blood. Particles may also be fluorinated to form stable compositions useful for $^{19}F$ imaging. Incorporating a paramagnetic metal species in the particles may reduce $^{19}F$ and proton relaxivity, thereby enhancing MRI, MRS, or MRSI.

Also disclosed are diagnostic compositions and methods of performing medical diagnostic procedures which involve administering to a warm-blooded animal a diagnostically effective amount of the above-described particles and then performing the medical diagnostic procedure.

DETAILED DESCRIPTION OF THE INVENTION

The present invention provides methods and compositions for improved medical diagnostic imaging. As used herein, medical diagnostic imaging includes magnetic resonance imaging ("MRI"), magnetic resonance spectroscopy ("MRS"), magnetic resonance spectroscopy imaging ("MRSI"), X-ray contrast imaging, and ultrasound imaging. The diagnostic imaging agents of the present invention are derived from calcium/oxyanion-containing particles.

As used herein, calcium/oxyanion-containing particles include calcium phosphate minerals, apatites, and apatite precursors of the general formula $Ca_nM_mX_rY_s$, where M is a paramagnetic metal ion, radiopaque metal ion, radioactive metal ion, or stoichiometric mixture of metal ions, X is a simple anion, Y is an oxyanion including tetrahedral oxyanions, protonated or unprotonated, carbonate, or mixtures thereof, m is from 0 to 10, n is from 1 to 10, s is $\geq 1$, and r is adjusted as needed to provide charge neutrality.

As used herein, apatite precursors include compounds within the scope of the above general formula having one or more amorphous phases which, when sintered, may become crystalline apatites.

Possible paramagnetic metal ions which can be used in the calcium/oxyanion-containing particles of the present invention include: chromium(III), manganese(II), iron(II), iron(III), praseodymium(III), neodymium(III), samarium(III), ytterbium(III), gadolinium(III), terbium(III), dysprosium(III), holmium(III), erbium(III), or mixtures of these with each other or with alkali or alkaline earth metals.

Certain radiopaque heavy metals, such as bismuth, tungsten, tantalum, hafnium, lanthanum and the lanthanides, barium, molybdenum, niobium, zirconium, and strontium may also be incorporated into particles to provide X-ray contrast. The radiopaque metals are incorporated into the calcium/oxyanion-containing particles in the same manner as paramagnetic metal ions.

Typical simple anions which can be used in the calcium/oxyanion-containing particles of the present invention include: $OH^-$, $F^-$, $Br^-$, $I^-$, $½[CO_3^{2-}]$, or mixtures thereof. The tetrahedral oxyanions used in the present invention may optionally include radiopaque metals or radioactive metals. Suitable tetrahedral oxyanions are nonoxidizing and stable to hydrolysis. Examples of suitable tetrahedral oxyanions for use in the present invention include: $PO_4^{3-}$, $AsO_4^{3-}$, $WO_4^{2-}$, $MoO_4^{2-}$, $VO_4^{3-}$, $SiO_4^{4-}$, and $GeO_4^{4-}$, and when stable, protnoated forms of these. Phosphate is a currently preferred tetrahedral oxyanion.

By controlling the particle size, organ specific imaging of the liver or gastrointestinal tract is obtained. When treated calcium/oxyanion-containing particles having a size in the range from about 5 nm to about 5 μm are injected into the vascular system, the particles collect in the liver or spleen (the RES system) because a normal function of these organs is to purify the blood of foreign particles. Once the particles have collected in the liver or spleen, these organs may be imaged by the desired medical diagnostic imaging technique.

Depending on the diagnostic imaging technique, calcium/oxyanion containing particles are treated to be paramagnetic, radiopaque, or echogenic. For example., paramagnetic metal species may be incorporated into the particles to improve magnetic resonance contrast, and radiopaque species may be incorporated to provide X-ray contrast. Particle density, and corresponding echogenic characteristics, can be controlled to impart low or high acoustic impedance relative to blood. The calcium/oxyanion-containing particles may also be fluorinated to form stable, nontoxic compositions useful for $^{19}F$ imaging. The presence of a paramagnetic metal species in these particles may reduce $^{19}F$ and proton relaxivity, thereby enhancing MRI, MRS, or MRSI.

The following discussion relates to apatites, a specific class of particles within the scope of the present invention. As used herein, the term apatite includes apatite and apatite precursors. Those skilled in the art will appreciate that the following discussion can be adapted to nonapatite calcium/oxyanion-containing particles within the scope of the present invention.

Preparation of Apatite Particles

Methods for preparing hydroxyapatite, having the formula $Ca_{10}(OH)_2(PO_4)_6$, are well known in the art. Apatites in which the $OH^-$ is replaced with simple anions, including $F^-$, $Br^-$, $I^-$, or $½[CO_3^{2-}]$, may be prepared by modifying the process for preparing hydroxyapatite. Apatite derivatives in which calcium is replaced by metal ions, such as paramagnetic, radiopaque, or radioactive metal ions, may also be prepared and used within the scope of the present invention. Useful apatites may also be prepared by replacing phosphate with oxyanions or tetrahedral anions containing radiopaque or radioactive metal species.

Stoichiometric pure hydroxyapatite has a Ca:P ratio of 1.67:1. The major impurity found in hydroxyapatite is tricalcium phosphate, $Ca_3(PO_4)_2$, known as "TCP". This impurity can be detected by deviation from the 1.67:1 Ca:P ratio (for large amounts of impurity) or by X-ray diffraction for impurity levels down to 1 percent.

Stoichiometric hydroxyapatite can prepared by adding an ammonium phosphate solution to a solution of calcium/ammonium hydroxide. To minimize the amount of TCP formed, it is important to have excess calcium throughout the addition process.

Apatite Particles for MRI Applications

The technique of MRI encompasses the detection of certain atomic nuclei (those possessing magnetic dipole moments) utilizing magnetic fields and radio-frequency radiation. It is similar in some respects to X-ray computed tomography ("CT") in providing a cross-sectional display of the body organ anatomy with excellent resolution of soft tissue detail. The technique of MRI advantageously avoids the use of ionizing radiation.

The hydrogen atom, having a nucleus consisting of a single unpaired proton, has the strongest magnetic dipole moment of any nucleus. Since hydrogen occurs in both water and lipids, it is abundant in the human body. Therefore, MRI is most commonly used to produce images based upon the distribution density of protons and/or the relaxation times of protons in organs and tissues. Other nuclei having a net magnetic dipole moment also exhibit a nuclear magnetic resonance phenomenon which may be used in magnetic resonance applications. Such nuclei include carbon-13 (six protons and seven neutrons), fluorine-19 (9 protons and 10 neutrons), sodium-23 (11 protons and 12 neutrons), and phosphorus-31 (15 protons and 16 neutrons).

In an MRI experiment, the nuclei under study in a sample (e.g. protons, $^{19}F$, etc.) are irradiated with the appropriate radio-frequency ("RF") energy in a controlled gradient magnetic field. These nuclei, as they relax, subsequently emit RF energy at a sharp resonance frequency. The resonance frequency of the nuclei depends on the applied magnetic field.

According to known principles, nuclei with appropriate spin when placed in an applied magnetic field (B, expressed generally in units of gauss or Tesla ($10^4$ gauss)) align in the direction of the field. In the case of protons, these nuclei precess at a frequency, F, of 42.6 MHz at a field strength of 1 Tesla. At this frequency, an RF pulse of radiation will excite the nuclei and can be considered to tip the net magnetization out of the field direction, the extend of this rotation being determined by the pulse, duration and energy. After the RF pulse, the nuclei "relax" or return to equilibrium with the magnetic field, emitting radiation at the resonant frequency. The decay of the emitted radiation is characterized by two relaxation times, $T_1$ and $T_2$. $T_1$ is the spin-lattice relaxation time or longitudinal relaxation time, that is, the time taken by the nuclei to return to equilibrium along the direction of the externally applied magnetic field. $T_2$ is the spin-spin relaxation time associated with the dephasing of the initially coherent precession of individual proton spins. These relaxation times have been established for various fluids, organs, and tissues in different species of mammals.

For protons and other suitable nuclei, the relaxation times $T_1$ and $T_2$ are influenced by the environment of the nuclei (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei or molecules (such as nitroxide radicals) which are paramagnetic. Chemical compounds incorporating paramagnetic nuclei or molecules may substantially alter the $T_1$ and $T_2$ values for nearby nuclei having a magnetic dipole moment. The extent of the paramagnetic effect of the given chemical compound is a function of the environment within which it finds itself.

In general, paramagnetic ions of elements with an atomic number of 21 to 29, 42 to 44 and 58 to 70 have been found effective as MRI contrasting agents. Examples of suitable paramagnetic ions include chromium(III), manganese(II), iron(II), iron(III), cobalt(II), nickel(II), copper(II), praseodymium(III), neodymium(III), samarium(III), gadolinium(III), dysprosium III), and ytterbium(III). Certain molecules, such as nitroxide radicals, also exhibit paramagnetic properties.

Paramagnetic metal ions may be incorporated into the apatite structure by replacement of calcium sites. Apatite doping in the range from about 1% to 100% is possible, depending upon the particular metal species. In most cases, apatite doping with metal ions in the range from about 1% to 25% is expected. Currently, the preferred metals from a toxicity and efficacy viewpoint are iron and manganese. With iron doped hydroxyapatite particles, any iron released from metabolized or solubilized particles would join the body's pool of iron, with calcium and phosphate also going to their respective body pools. Manganese is preferred because of its higher relaxivity properties and affinity for liver tissue. Moreover, the liver has a clearance mechanism for manganese, thereby reducing residual toxicity.

Metal doped hydroxyapatite can be prepared by mixing a basic (pH 10–12) phosphate solution with a calcium/paramagnetic metal solution at native pH. It has been found that the paramagnetic ions incorporated into the apatite particle tend to oxidize during particle synthesis. To prevent metal oxidation, manufacturing techniques have been developed to minimize the amount of oxygen in the aqueous reactant solutions. For example, two such manufacturing techniques are (1) synthesis at high temperature, such as 100° C. and (2) degassing the aqueous reactant solutions with an inert gas such as argon, nitrogen, or helium. An unexpected benefit of these techniques is the ability to prepare smaller particles, in the range from 50 nm to about 1 μm.

Antioxidants, such as gentisic acid and ascorbic acid, added during apatite particle synthesis may also be used to prevent metal ion oxidation. Reducing agents, such as $NaBH_4$, have been found to reduce metal ions that are unintentionally oxidized during apatite particle synthesis.

Paramagnetic apatite particles may also be prepared by adsorbing paramagnetic metal ions onto the particle surface. For example, manganese can be surface-adsorbed to hydroxyapatite particles by taking a slurry of hydroxyapatite, adding $Mn(NO_3)_2$ and applying energy, such as ultrasonic power or heat, to the resulting mixture. The resulting mixture can be separated by either centrifugation and decantation or by filtration. The resulting solid is washed with large amounts of water to remove excess manganese. The same procedure may be used with other paramagnetic cations. The amount of manganese adsorbed onto the particle surface, as a percentage of the total calcium in the particle, is in the range from about 0.1% to about 10%. Such particles exhibit very high relaxivities and rapid liver enhancement in magnetic resonance imaging studies.

Paramagnetic metal species may also be adsorbed onto apatite particle surfaces through the use of bifunctional coating agents. Examples of possible bifunctional coating agents are chelating agents having one or more phosphonate groups capable of adsorption to the apatite particle surface. One currently preferred bifunctional coating agent is the functionalized polyphosphonate diethylenetriaminepenta(methylenephosphonic acid), abbreviated DETAPMDP, having the following structure:

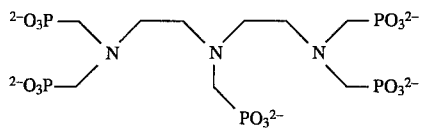

Once adsorbed to the apatite particle surface, the bifunctional coating agent may form complexes with paramagnetic metal ions. These particles also exhibit very high relaxivities and rapid liver enhancement in magnetic resonance imaging studies.

In some cases, the concentration of nuclei to be measured is not sufficiently high to produce a detectable MR signal. For instance, since $^{19}F$ is present in the body in very low concentration, a fluorine source must be administered to a subject to obtain a measurable MR signal. Signal sensitivity is improved by administering higher concentrations of fluorine or by coupling the fluorine to a suitable "probe" which will concentrate in the body tissues of interest. High fluorine concentration must be balanced against increased tissue toxicity. It is also currently believed that a fluorine agent should desirably contain magnetically equivalent fluorine atoms in order to obtain a clear, strong signal.

Fluoroapatites, useful as $^{19}F$ imaging agents, are prepared by replacing the $OH^-$ with stoichiometric or nonstoichiometric quantities of $F^-$. Fluoroapatites may also be synthesized with organic phosphate esters using the procedures described by M. Okazaki, "Fluoridated Hydroxyapatites Synthesized With Organic Phosphate Ester," *Biomaterials*, Vol. 12, pp. 46–49, (1991). It is currently believed that all of the fluorine atoms in fluoroapatite are chemically and magnetically equivalent. Since fluoroapatite has a high molar content of identical fluorine atoms, it may be advantageously used as a low concentration $^{19}F$ MRI agent. Fluoroapatite may also be doped with paramagnetic metal species, as described above, to reduce $^{19}F$ and proton relaxivity, thereby enhancing MRI, MRS, or MRSI.

Apatite Particles for X-ray Contrast Applications

The apatite particles described herein may also be adapted for delivery of radiopaque species into the body for X-ray contrast. Typical radiopaque species which may be incorporated into the apatite particles include heavy metals, iodine, or iodinated XRCM.

Iodoapatites are prepared by replacing the $OH^-$ of hydroxyapatite with stoichiometric or non-stoichiometric quantities of $I^-$. Because iodine is substantially radiopaque, iodoapatites may be used as X-ray contrast media ("XRCM"). By controlling the particle size, iodoapatite particles may be used to image the liver or spleen of the RES or the gastrointestinal tract.

Commercially available XRCM, such as Ioversol, my be incorporated in apatite particles during particle precipitation. In the case of hydroxyapatite particles, the XRCM may be included in either the phosphate or calcium solution. The XRCM is preferably in sufficiently high concentration that upon precipitation of the apatite particles, the XRCM has a concentration in the particles in the range from about 1% to about 25%, by weight.

Certain radiopaque heavy metals, such as bismuth, tungsten, tantalum, hafnium, lanthanum and the lanthanides, barium, molybdenum, niobium, zirconium, and strontium may also be incorporated into apatite particles to provide X-ray contrast.

Apatite Particles for Ultrasound Applications

Ultrasound is a medical diagnostic technique in which sound waves are reflected differently against different types of tissue, depending upon the acoustic impedance of these tissues. There is interest in being able to use some type of contrast agent to obtain an amplification of specific organs. Hydroxyapatite particles may be made echogenic by either of two mechanisms: (1) reflection off high density hydroxyapatite particles or (2) reflection off air trapped within low density hydroxyapatite particles.

Since hydroxyapatite is a porous material, small pockets of gas within the particles render them echogenic, with an impedance less than blood. An ultrasound contrast media would be provided in a two-vial kit form: one vial containing dry hydroxyapatite and the other vial containing a diluent.

For example, appropriately sized particles would be synthesized using a volatile organic solvent and then dried by freeze-drying or lyophilization. The resulting dried particles would have pores filled with gas. Just prior to use, a second vial containing a specific volume of a sterile aqueous diluent, such as isotonic saline and/or buffer, can be aspirated and added to the vial of the dried hydroxyapatite. The slurry is then mixed and immediately injected. Enough gas remains in the pores to provide echogenicity in vivo for ultrasound contrast.

Alternatively, carbonate can be incorporated into the hydroxyapatite matrix. Appropriately sized particles would be dried as described above. The diluent vial would contain a weak biocompatible acid such as, but not limited to, acetic acid, citric acid, $NaH_2PO_4$, etc. The diluent and hydroxyapatite particles are mixed to allow the acid to react with the carbonate and form carbon dioxide in the particle pores according to equation A, below. The mixture would then be injected in vivo and ultrasound imaging of the desired vasculature would proceed.

$$CO_3^{2-} - 2H^+ \rightarrow CO_2 + H_2O$$

Echogenic hydroxyapatite particles with an impedance higher than blood may also be prepared. Prolonged heating or sintering at high temperatures can render hydroxyapatite, with or without additives, into a hardened, less porous material that is denser than blood. Dense hydroxyapatite particles can transmit sound faster than blood., thereby providing an echogenic material having an impedance higher than blood.

High impedance ultrasound contrast media may be provided as either a pre-mixed single vial formulation or a two-vial kit form. Appropriately sized particles formed and heated at optimum conditions would ultimately be formulated with a biocompatible aqueous diluent such as, but not limited to, isotonic saline and/or a buffer.

Although the foregoing discussion has focused on the use of treated hydroxyapatite particles for ultrasound contrast, it will be appreciated that other apatite particles may also be treated and used as ultrasound contrast agents.

Controlling the Particle Size and Aggregation

Various techniques are available to control the apatite particle size. For example, slower addition rates (introduction of the precipitating anion or cation), faster stirring, higher reaction temperatures, and lower concentrations generally result in smaller particles. In addition, sonication during precipitation, turbulent flow or impingement mixers, homogenization, and pH modification may be used to control particle size. Other means, such as computer controlled autoburets, peristaltic pumps, and syringes, may be used to control the release of precipitating ions to produce smaller particles.

Due to the small size and nature of apatite particles, they tend to aggregate. Particle aggregation may be reduced by coating the particles. Although the reasons apatite particles aggregate is not fully understood, it has been found that several different coating agents are able to inhibit particle aggregation. For example, apatite particles may be stabilized by treatment with coating agents such as di- and polyphosphonate-containing compounds, such as 1-hydroxyethane-1,1-diphosphonate (HEDP), pyrophosphate, aminophosphonates; carboxylates and polycarboxylate-containing compounds such as oxalates and citrates; alcohols and polyalcohol-containing compounds; phosphates and polyphosphate-containing compounds; sulfates and sulfate-containing compounds; sulfonates and sulfonate-containing compounds; and biomolecules such as peptides, proteins, antibodies, and lipids. Such coating agents stabilize the small apatite particles by reducing further particle growth and promoting particle suspension.

Stabilized apatite particles are desirable for in vivo use as medical diagnostic imaging agents. Apatite particle can also be stabilized by addition of small amounts of calcium sequestering anions, such as citrate and oxalate. Such anions, which coordinate calcium, may effectively stabilize small apatite particles.

When used in magnetic resonance imaging, particle relaxivity is enhanced by allowing more water accessible to the particle surface. By limiting particle size and. increasing the available surface area, improved relaxivity is observed.

In addition to the coating agents identified above, conventional particle coating techniques may also be used in the manufacturing processes of the present invention. Typical coating techniques are identified in International Publication Numbers WO 85/02772, WO 91/02811, and European Publication Number EP 0343934, which are incorporated by reference.

For instance, agglomerated particles may be disrupted by mechanical or chemical means and then coated with polymers such as carbohydrates, proteins, and synthetic polymers. Dextran having a molecular weight in the range from about 10,000 to about 40,000 is one currently preferred coating material. Albumin and surfactants, such as TWEEN®80, have also been used to reduce particle aggregation. One common characteristic of useful apatite coating agents is their ability to modify the particle surface charge, or zeta potential.

The currently preferred mechanical means for disrupting or subdividing agglomerated particles is sonication, but other means such as heating, other forms of particle energization, such as irradiation, and chemical means, such as pH modification or combinations of these types of treatment, such as pH modification combined with sonication may be used.

Functionalized Apatite Particles

Apatite particles may be prepared with coating agents containing reactive functional groups such as amine, active ester, alcohol, and carboxylate. Such functional groups may be used to couple apatite particles to paramagnetic metal chelates, to organ or tissue specific peptides or proteins, and to antibodies. An example of one possible coating agent having a reactive functional group is the following HEDP derivative:

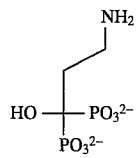

Those skilled in the art will appreciate that other coating agents, modified to contain various reactive functional groups, may be used in the present invention.

Diagnostic Pharmaceutical Formulations

The apatite particles of this invention are preferably formulated into diagnostic compositions for parenteral. administration. For example, parenteral formulations advantageously contain a sterile aqueous solution or suspension of treated apatite particles according to this invention. Various techniques for preparing suitable pharmaceutical solutions and suspensions are known in the art. Such solutions also may contain pharmaceutically acceptable buffers and, optionally, electrolytes such as sodium chloride. Parenteral compositions may be injected directly or mixed with a large volume parenteral composition for systemic administration.

The diagnostic compositions of this invention are used in a conventional manner in magnetic resonance, X-ray, and ultrasound procedures. The diagnostic compositions are administered in a sufficient amount to provide adequate visualization, to a warm-blooded animal either systemically or locally to an organ or tissues to be imaged, then the animal is subjected to the medical diagnostic procedure. Such doses may vary widely, depending upon the diagnostic technique employed as well as the organ to be imaged. The required dosage, particularly in the field of MRI and X-ray contrast, are well understood by those skilled in the art.

The following examples are offered to further illustrate the present invention. These examples are intended to be purely exemplary and should not be viewed as a limitation on any claimed embodiment.

EXAMPLE 1

Preparation of Hydroxyapatite

A calcium nitrate solution was prepared by adding 1.18 g $Ca(NO_3)_2 \cdot 4H_2O$ to 20 mL deionized water such that the final $[Ca^{2+}]=0.25$ M. The calcium nitrate solution pH was adjusted to a pH of 11 with ammonium hydroxide. An ammonium phosphate solution was prepared by adding 0.396 g $(NH_4)_2HPO_4$ to 5 mL of deionized water. The pH of the ammonium phosphate solution was adjusted to a pH of 11 with ammonium hydroxide. The ammonium phosphate solution was injected into the calcium nitrate solution and vigorously stirred. The resulting precipitated particles were examined under a microscope and estimated to have particle sizes greater than 10 μm.

EXAMPLE 2

Preparation of Hydroxyapatite

Hydroxyapatite particles were prepared according to the procedure of Example 1, except that the pH of the calcium nitrate solution was not adjusted to pH 11. The ammonium phosphate solution was injected into the calcium nitrate solution and vigorously stirred. The resulting precipitated particles were examined under a microscope and estimated to have particle sizes greater than 10 μm.

EXAMPLE 3

Preparation of Hydroxyapatite

A calcium nitrate solution was prepared by adding 0.68 g $Ca(NO_3)_2 \cdot 4H_2O$ to 5 mL deionized water such that the $[Ca^{2+}]=0.58$ M. The calcium nitrate solution pH was adjusted to a pH of 11 with ammonium hydroxide. An ammonium phosphate solution was prepared by adding 0.22 g $(NH_4)_2HPO_4$ to 10 mL of deionized water such that the $[HPO_4^{2-}]=0.17$ M. The pH of the ammonium phosphate solution was adjusted to 11 with ammonium hydroxide. The ammonium phosphate solution was dripped into a vigorously stirred calcium nitrate solution over 30 minutes. After mixing, the final $[Ca^{2+}]=0.19$ M. The resulting precipitated particles were examined under a microscope and estimated to have particle sizes of approximately 1 μm.

EXAMPLE 4

Preparation of Hydroxyapatite Doped with a Paramagnetic Metal Ion

A metal ion solution was prepared by adding 1.18 g $Ca(NO_3)_2 \cdot 4H_2O$ and 0.202 g $Fe(NO_3)_3 \cdot 9H_2O$ to 20 mL deionized water. An ammonium phosphate solution was prepared by adding 0.396 g $(NH_4)_2HPO_4$ to 5 mL of deionized water. The pH of the ammonium phosphate solution was adjusted to 11 with ammonium hydroxide. The ammonium phosphate solution was injected into the metal ion solution and vigorously stirred. The resulting precipitated particles were examined and found to have particle sizes greater than 10 μm.

EXAMPLE 5

Preparation of Fluoroapatite

Fluoroapatite is prepared by mixing 5 mL of a 0.58 M solution of calcium fluoride with 10 mL of a 0.17 M ammonium phosphate solution at native pH. The calcium fluoride solution is dripped into a vigorously stirred ammoniumphosphate solution over 30 minutes. The resulting precipitated particles are examined under a microscope and estimated to have particle sizes of approximately 1 μm.

EXAMPLE 6

Preparation of Fluoroapatite

Fluoroapatite is prepared by mixing 5 mL of a 0.58 M solution of calcium nitrate with 10 mL of solution containing 0.17 M ammonium phosphate and 0.17 M ammonium fluoride. The calcium nitrate solution is dripped into a vigorously stirred ammoniumphosphate and ammonium fluoride solution over 30 minutes. The resulting precipitated particles are examined under a microscope and estimated to have particle sizes of approximately 1 μm.

EXAMPLE 7

Preparation of Fluoroapatite Doped with a Paremagnetic Metal Ion

Fluoroapatite doped with a paramagnetic metal ion is prepared according to the procedure of Example 5, except that the calcium fluoride solution also contains 0.058 M manganese nitrate. The calcium fluoride/manganese nitrate solution is dripped into a vigorously stirred ammonium phosphate solution over 30 minutes. The resulting precipitated particles are examined under a microscope and estimated to have particle sizes of approximately 1 μm.

EXAMPLE 8

Preparation of Iodoapatite

Iodoapatite is prepared by mixing 5 mL of a 0.58 M solution of calcium iodide with 10 mL of a 0.17 M ammonium phosphate solution at native pH. The calcium iodide solution is dripped into a vigorously stirred ammonium phosphate solution over 30 minutes. The resulting precipitated particles are examined under a microscope and estimated to have particle sizes of approximately 1 μm.

EXAMPLE 9

Preparation of Iodoapatite

Iodoapatite is prepared by mixing 5 mL of a 0.58 M solution of calcium nitrate with 10 mL of solution containing 0.17 M ammonium phosphate and 0.17 M ammonium iodide. The calcium nitrate solution is dripped into a vigorously stirred ammonium phosphate and ammonium iodide solution over 30 minutes. The resulting precipitated particles are examined under a microscope and estimated to have particle sizes of approximately 1 μm.

EXAMPLE 10

Preparation of Hydroxyapatite Doped with an XRCM

Hydroxyapatite particles doped with iothalamate meglumine, an ionic XRCM, are prepared according to the procedure of Example 3, except that the calcium nitrate solution also contains 0.058 M iothalamate meglumine salt. Iothalamate has the following structure:

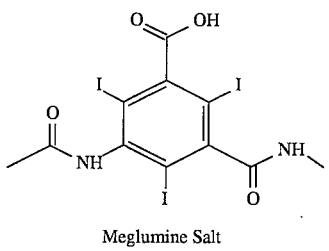

Meglumine Salt

The ammonium phosphate solution is dripped using an autoburet into a vigorously stirring solution of calcium nitrate and iothalamate meglumine over 30 minutes. The resulting precipitated particles are examined under a microscope and estimated to have submicron particle sizes.

EXAMPLE 11

Preparation of Hydroxyapatite Doped with a Radiopaque Heavy Metal

Hydroxyapatite particles doped with tungsten are prepared according to the procedure of Example 3, except that the ammonium phosphate solution also contains 0.116 M sodium tungstate, $Na_2WO_4$. The ammoniumphosphate and sodium tungstate solution is dripped using an autoburet into a vigorously stirred solution of calcium nitrate over 30 minutes. The resulting precipitated particles are examined under a microscope and estimated to have submicron particle sizes.

EXAMPLE 12

Preparation of Hydroxyapatite Doped with Carbonate

Carbonate-doped hydroxyapatite particles are prepared according to the procedure of Example 3, except that calcium carbonate was used instead of calcium nitrate. The ammonium phosphate solution is dripped using a computer controlled autoburet into a vigorously stirred calcium carbonate solution over 30 minutes. The resulting precipitated particles were examined under a microscope and estimated to have submicron particle sizes.

EXAMPLE 13

Preparation of High Density Hydroxyapatite

Hydroxyapatite particles are prepared according to the procedure of Example 3 and sintered at a temperature in the range from about 200° C. to about 1100° C. to harden and densify the particles. The dense particles can then be mixed with a suitable pharmaceutical carrier and administered as a high acoustic impedance ultrasound contrast media.

EXAMPLE 14

Preparation at 100° C. of Hydroxyapatite

An ammonium phosphate solution was prepared by dissolving 10.56 grams $(NH_4)_2HPO_4$ in 200 mL of D.I. water. To this was added 100 mL of concentrated $NH_4OH$ with stirring. A white precipitate formed which was dissolved by addition of 150 mL of $H_2O$. This solution was stirred for 3 hours at room temperature and then added dropwise (over 2 hours) via a peristaltic pump (Masterflex) to a 1000 mL three-neck round bottom flask fitted with a dry ice/isopropanol condenser on top of a standard water-jacketed condenser containing a solution of 31.5 grams $Ca(NO_3)_2 \cdot 4H_2O$ in 500 mL of $H_2O$ in boiling water stirred rapidly with a mechanical stirrer. Reflux was continued for two hours after addition was complete and the mixture was allowed to cool to room temperature with stirring overnight. The reaction mixture was centrifuged at 2300 rpm and the nearly-clear supernatant discarded. The resulting white, pelleted solid was slurried with water and completely broken up by means of a vortex mixer. The mixture was again centrifuged and the cloudy supernatant collected. The washing was repeated two separate times. All three washings were saved as was the remaining solid in the centrifuge tubes. The calcium/phosphorous ratio and particle size of the washed particles is summarized belows:

|  | Ca/P Ratio | Particle size (std. dev.) |
|---|---|---|
| wash 1: | 1.65 | 663 (456) nm |
| wash 2: | 1.67 | 351 nm, 1853 nm† |
| wash 3: | 1.67 | 190 nm, 1069 nm† |

†Bimodal distribution noted, no standard deviations given.

EXAMPLE 15

Preparation at 100° C. of Hydroxyapatite Doped with Mn(II)

This material was prepared according to the procedure of Example 14 except that a Mn(II) (as $Mn(NO_3)_2 \cdot 6H_2O$) was substituted mole-for-mole for Ca. For example, to synthesize 5% Mn incorporated into HA:

10.56 grams $(NH_4)_2HPO_4$ was dissolved in 200 mL of D.I. water. To this was added 100 mL of concentrated $NH_4OH$ with stirring. A white precipitate formed which was dissolved by addition of 150 mL of $H_2O$. This solution was stirred for 3 hours at room temperature and then added dropwise (over 2 hours) via a peristaltic pump (Masterflex) to a 1000 mL three-neck round bottom flask fitted with a dry ice/isopropanol condenser on top of a standard water-jacketed condenser containing a solution of 1.27 grams $Mn(NO_3)_2 \cdot 6H_2O$ and 29.9 grams $Ca(NO_3)_2 \cdot 4H_2O$ in 500 mL of $H_2O$ in boiling water stirred rapidly with a mechanical stirrer. Reflux was continued for two hours after addition was complete and the mixture was allowed to cool to room temperature with stirring overnight. The reaction mixture was centrifuged at 2300 rpm and the nearly-clear supernatant discarded. The resulting off-white, pelleted solid was slurried with water and completely broken up by means of a vortex mixer. The mixture was again centrifuged and the cloudy supernatant collected. The washing procedure was repeated two times. All three washings were saved as was the remaining solid in the centrifuge tubes. The particle size of the particles in the supernatant increased and the percentage of particles in the supernatant decreased (i.e., less cloudy supernatant). Solids from supernatants could be concentrated by further centrifugation at 7000 rpm. The average particle size was 449 nm with a standard deviation of 171 nm.

EXAMPLE 16

Preparation at 100° C. of Hydroxyapatite particles Doped with Mn and treated with HEDP Manganese containing hydroxyapatite particles were prepared by the following general procedure (Mn/Ca mole ratios of <0.33 can be used):

A solution containing 6.5 g of $(NH_4)_2HPO_4$ in 120 mL of deionized water was treated with 60 mL of concentrated ammonium hydroxide, $NH_4OH$ followed by 90 mL of D.I. water. The resulting mixture was stirred at room temperature for 3 hours.

Into a 1L 3-neck round bottom flask equipped with a water cooled/low temperature condenser sequence (dry ice/isopropanol bath), mechanical stirrer and rubber septum were placed 18.3 g of $Ca(NO_3)_2 \cdot 4H_2O$ and 0.7 g of $Mn(NO_3)_2 \cdot 6H_2O$ in 468 mL of D.I. water (Ca/Mn mole ratio=19/1, Ca+Mn=0.081 moles). The resulting solution was heated to reflux. The phosphate/hydroxide mixture was then added dropwise over approximately one hour with a peristaltic addition pump. The reaction mixture was cooled to room temperature and stirred overnight. The solution was then treated with 0.54 M HEDP (pH 6.6, 1–1.2 Ca/HEDP mole ratio) and stirred at room temperature for one hour.

The reaction mixture was then divided among six 50 mL plastic centrifuge tubes and centrifuged for 15 minutes at 2400 rpm. The procedure was repeated with the remainder of the reaction mixture. The almost clear supernatant was discarded and the solid in each tube resuspended to 50 mL of volume with D.I. water and re-centrifuged. The milky wash was set aside and the solid washed twice more. The three washes were combined and then centrifuged at 7000 rpm for 30 minutes. The particles remained pelleted and the clear supernatant was decanted. The solid was resuspended in water and re-centrifuged three more times at 7000 rpm discarding the supernatant after each washing. After the centrifuge workup the solid particles were resuspended in 20–30 mL of D.I. water and then subjected to routine analysis.

Characterization of the particle suspension gave the following results:
size (average diameter, nm): 258
relaxivity (mMolar$^{-1}$ sec$^{-1}$): 3.05
[Mn] (mole/liter): 0.11
[Ca] (mole/liter): 3.29
% Mn (mole % relative to Ca): 3.35
In magnetic resonance imaging studies, a 45% enhancement of the liver was observed 4 hours post injection at a dose of 10 μmoles Mn/Kg animal body weight.

EXAMPLE 17

Preparation at room temperature of Hydroxyapatite particles Doped with Mn and treated with HEDP Manganese containing hydroxyapatite particles were prepared by the following general procedure. A procedure is described for particles containing 10% Mn but other percentages are also applicable.

Into a 1L erlenmeyer flask were placed 10.5 g of $(NH_4)_2HPO_4$, 100 mL of concentrated $NH_4OH$ and 350 mL of D.I. water. The mixture was stirred for two hours with a continuous heavy argon flow (degassing). In a separate 1L erlenmeyer flask were placed 28.9 g of $Ca(NO_3)_2 \cdot 4H_2O$ and 2.4 g of $Mn(NO_3)_2 \cdot 6H_2O$ in 400 mL of D.I. water. The metal nitrate solution was degassed with argon for 2 hours. The phosphate solution was then added dropwise to the rapidly stirred metal nitrate mixture over two hours with a peristaltic pump. A continuous argon flow was maintained throughout the course of the reaction. The reaction mixture was stirred for an additional two hours after the addition was complete.

A solution of 8.3 g of a 60% solution HEDP (acid form) in 25 mL of D.I. water was degassed for 30 minutes then added in one aliquot to the hydroxyapatite mixture. The resulting slurry was stirred for 15 minutes. The entire reaction mixture was centrifuged at one time at 2400 rpm for 15 minutes. The supernatant was discarded and the solid residue in each tube resuspended in water. The slurry was re-centrifuged at 2400 rpm and the milky supernatant was collected. The solid was resuspended twice more and centrifuged at 2400 rpm. The three washes were combined and centrifuged at 7000 rpm for 30 minutes. The solid pellet was washed/centrifuged three times and the supernatants discarded. After washing, the solid pellet was suspended in 30 mL of D.I. $H_2O$.

Characterization of the particulate suspension produced the following results:
size (average diameter, nm): 229
relaxivity (mMolar-1 sec-1): 29.4
[Mn] (mole/liter): 0.027
[Ca] (mole/liter): 0.377
% Mn (mole % relative to Ca): 6.71
In magnetic resonance imaging studies, a 45% enhancement of the liver was observed immediately post injection at a dose of 10 μmoles Mn/Kg animal body weight.

EXAMPLE 18

Preparation at room temperature of Hydroxyapatite Doped with 10%Mn(II), Modified by Surface- Adsorbed Mn(II) and HEDP Addition An ammonium phosphate solution was prepared by dissolving 5.3 grams $(NH_4)_2HPO_4$ in 175 mL of D.I. water. To this was added 50 mL of concentrated $NH_4OH$ with stirring. This solution was degassed for 2 hours (argon bubbling) with stirring and then added dropwise (over 2 hours) via a peristaltic pump (Masterflex) to a solution of 1.27 grams $Mn(NO_3)_2 \cdot 6H_2O$ and 14.5 grams $Ca(NO_3)_2 \cdot 4H_2O$ in 200 mL of $H_2O$ that had also been deaerated for 2 hours with argon as it was stirred rapidly with a mechanical stirrer. Argon bubbling was continued during the addition. The reaction mixture was stirred for an additional 2 hours as the Ar bubbling continued. 1.27 g $Mn(NO_3)_2 \cdot 6H_2O$ in 25 mL of deaerated $H_2O$ was added in one portion to the reaction slurry, followed, after 15 minutes, by 4.3 grams of a 60% HEDP solution in water dissolved in 10 mL of deaerated $H_2O$. The reaction mixture was centrifuged at 2300 rpm and the nearly-clear supernatant discarded. The resulting white, pelleted solid was slurried with water and completely broken up by means of a vortex mixer. The mixture was again centrifuged and the cloudy supernatant collected. The washing was repeated two separate times. All three washings were saved as was the remaining solid in the centrifuge tubes.

In magnetic resonance imaging studies, a 30% enhancement of the liver was observed immediately post injection at a dose of 10 μmoles Mn/Kg animal body weight.

EXAMPLE 19

Preparation at 100° C. of Hydroxyapatite Particles Modified by Surface-Adsorbed Mn(II) and HEDP Addition Into a 250 mL erlenmeyer flask were placed 6.3 g of $(NH_4)_2HPO_4$ in 120 mL of D.I. water. Concentrated $NH_4OH$ (60 mL) was added to the mixture followed by 90 mL of D.I. water. The solution was stirred at room temperature for four hours.

Into a 1L 3-neck round bottom flask equipped with a water cooled and low temperature condenser sequence (dry ice/isopropanol), mechanical stirrer, and rubber septum were placed 19.0 g of $Ca(NO_3)_2 \cdot 4H_2O$ in 468 mL of D.I. $H_2O$. The mixture was heated to reflux and the phosphate/ammonium hydroxide solution added dropwise with a peristaltic pump and rapid stirring over one hour. The heating was removed when the addition was complete. The reaction mixture was cooled to room temperature then stirred overnight.

The pH of the hydroxyapatite slurry was adjusted from 9.50 to 8.70 with 80mL of 0.5 N HCl. 2.1 g of $Mn(NO_3)_2 \cdot 6H_2O$ in 5 mL of $H_2O$ was added to the hydroxyapatite mixture and stirred for four hours. The reaction mixture became light brown in color. A solution of HEDP (0.54 M, Ca/HEDP mole ratio=1.1) was added and the resulting reaction mixture stirred at room temperature for 3 hours. The color of the slurry became purple/brown.

The reaction mixture was divided among six 50 mL plastic centrifuge tubes and centrifuged for 15 minutes at 2400 rpm. The supernatant was deep purple and clear. The solid residue was washed/centrifuged three times with 50 mL volumes of water per tube and the three washes combined. The combined washes were centrifuged at 7000 rpm for 20 minutes. The solid pellets were washed/centrifuged three additional times discarding the supernatant after each centrifuge run. The white solid residue was suspended in 15 mL of D.I. $H_2O$ then subjected to routine analyses.

The analyses of the manganese adsorbed hydroxylapatite slurry gave the following results:
size (average diameter, nm): 259
relaxivity (mMolar$^{-1}$ sec$^{-1}$): 13.8
[Mn] (mole/liter): 0.010
[Ca] (mole/liter): 1.60
% Mn (mole % relative to Ca): 0.66

EXAMPLE 20

Preparation at Room Temperature of Hydroxyapatite Doped with 104 Mn(II), Modified by Sequential Addition of Mn(II) and HEDP With Washings Between Steps The general procedure is the same as in Example 18. Before addition of the additional $Mn(NO_3)_2 \cdot 6H_2O$, however, the reaction mixture was pH adjusted from 9.8 to a lower pH (7.5–9.5) and the mixture then centrifuged, the resulting solid washed with D.I. water, the $Mn(NO_3)_2 \cdot 6H_2O$ added with, stirring under argon bubbling, the resultant mixture centrifuged and the solid washed with water. In the final step the HEDP was added to the slurried solid and then the excess washed away with the supernatant during centrifugation.

In the preparation where the pH was adjusted to 9.5, 5.3 grams $(NH_4)_2HPO_4$ was dissolved in 175 mL of D.I. water. To this was added 50 mL of concentrated $NH_4OH$ with stirring. This solution was degassed for 2 hours (argon bubbling) with stirring and then added dropwise (over 2 hours) via a peristaltic pump (Masterflex) to a solution of 1.27 grams $Mn(NO_3)_2 \cdot 6H_2O$ and 14.5 grams $Ca(NO_3)_2 \cdot 4H_2O$ in 200 mL of $H_2O$ that had also been deaerated for 2 hours with argon as it was stirred rapidly with a mechanical stirrer. Argon bubbling was continued during the addition. The reaction mixture was stirred for an additional 2 hours as the argon bubbling continued. The pH of the reaction mixture was adjusted from 9.8 to 9.0 with 3 N HCl with rapid stirring and argon bubbling.

1.27 g $Mn(NO_3)_2 \cdot 6H_2O$ in 25mL of deaerated $H_2O$ was added in one portion to the reaction slurry, followed, after 60 minutes, by centrifugation and one washing of the resultant solid (via vortex mixing and recentrifugation). The solid was suspended in water and treated with 4.3 grams of a 60% HEDP solution in water dissolved in 10 mL of deaerated $H_2O$. After 15 minutes the reaction mixture was centrifuged at 2300 rpm and the nearly-clear supernatant discarded. The resulting white, pelleted solid was slurried with water and completely broken up by means of a vortex mixer. The mixture was again centrifuged and the cloudy supernatant collected. The washing was repeated two separate times. All three washings were combined and the solids from those washings pelleted by centrifugation at 7000 rpm. The resulting pellet was washed with water 3 times by suspension followed by centrifugation at 7000 rpm. The particles were analyzed and found to have an average particle size of 251 nm and a relaxivity, $R_1$=25 mM$^{-1}$sec$^{-1}$.

EXAMPLE 21

Preparation at 100° C. of Hydroxyapatite Particles Modified by Surface-Adsorbed Mn, Purified, then Treated with HEDP Calcium hydroxyapatite particles were prepared by the following procedure:

A solution containing 6.5 g of $(NH_4)_2HPO_4$ in 120 mL of D.I. water was treated with 60 mL of concentrated $NH_4OH$ followed by 90 mL of D.I. water. The resulting solution was stirred for 3 hours at room temperature.

Into a 3-neck 1L round bottom flask equipped with a water cooled and low temperature condenser sequence ice/isopropanol), mechanical stirrer and rubber septum were placed 19.4 g of $Ca(NO_3)_2 \cdot 4H_2O$ in 468 mL of D.I. water. The solution was heated to reflux. The phosphate mixture was added to the rapidly stirred calcium nitrate solution dropwise with a peristaltic pump over one hour. The heal; was removed when the addition was complete and the reaction mixture cooled to room temperature. The hydroxylapatite slurry was stirred overnight at room temperature.

The pH of the reaction mixture was decreased from 9.53 to 8.50 with 169 ml of 1N HCl. Manganese nitrate,, $Mn(NO_3)_2 \cdot 6H_2O$ (2.10 g) was added to the hydroxyapatite mixture and stirred for 1 hour and 15 minutes. The color of the slurry became pale tan. The mixture was then centrifuged at 2400 rpm for 15 minutes. The clear colorless supernatant was discarded and the solid washed/centrifuged with 3–50 mL aliquots of water at 2400 rpm for 15 minutes per run. Half of the solid residue was suspended in 200 mL of D.I. water and stirred vigorously then placed in an ultrasonic bath for 10 minutes to break apart any large clumps. The solid slurry was then treated with 0.54 M HEDP (Ca/HEDP mole ratio=1.2) and stirred for 1.5 hours. The color of the mixture became pale pink/purple. The remaining half of the solid hydroxyapatite pellet was suspended in 200 mL of D.I. $H_2O$ and set aside for characterization and analyses.

The HEDP treated hydroxyapatite fraction was divided, among six 50 mL plastic centrifuge tubes and centrifuged for 15 minutes at 2400 rpm. The supernatant was deep purple and slightly cloudy. The solid residue was suspended in $H_2O$ and centrifuged at 7000 rpm for 30 minutes. The supernatant was discarded and the solid pellet washed/centrifuged three more times at 7000 rpm. The purified hydroxyapatite was suspended in approximately 30 mL of D.I. water then characterized. The results of the analyses are listed below.

| | HEDP treated | untreated |
|---|---|---|
| size (average diameter, nm): | 216 | 34,100 |
| relaxivity (mMolar$^{-1}$ sec$^{-1}$): | 38.3 | 0.78 |
| [Mn] (mole/liter): | 0.0025 | 0.016 |
| [Ca] (mole/liter): | 0.170 | 0.638 |
| % Mn (mole % relative to Ca): | 1.44 | 2.45 |

In magnetic resonance imaging studies, a 25% enhancement of the liver was observed immediately post injection at a dose of 10 μmoles Mn/Kg animal body weight.

EXAMPLE 22

Preparation of Mn-Doped Hydroxyapatite Particles Having a Functionalized Coating Agent This example describes the general preparation of hydroxyapatite particles having a functionalized coating agent. The particles are prepared by adding 0.1–100 mole % of an appropriate coating agent to a slurry of Mn(II) substituted hydroxyapatite with 0.1–100 mole % Mn based on the Ca used in the reaction. The mixture is stirred from 1 to 360 minutes at temperatures in the range from 4° C. to 100° C. and the solid separated from the supernatant by centrifugation. The resulting solid is collected or subjected to repeated washings with water to remove excess ions and coating agent. The solid, after resuspension in water, may be treated with a metal salt (0.01–10 mole % based on Ca in the preparation). This is especially appropriate if the coating agent contains a pendant chelating group to capture and hold tightly the metal (when subjected to in vitro and/or in vivo solutions). The resultant solid is separated by centrifugation and washed 3 times with water to remove loosely attached coating agent or free metal/coating agent complex.

EXAMPLE 23

Preparation of Hydroxyapatite Particles treated with Diethylenetriamine-penta(methylenephosphonic acid) Followed by Surface Adsorption of Mn Calcium hydroxyapatite was prepared by the following procedure then treated with the functionalized polyphosphonate, diethylenetriamine-penta(methylenephosphonic acid), abbreviated DETAPMDP and having the following structure:

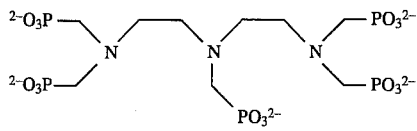

A basic ammoniumphosphate solution was prepared using 6.34 g of $(NH_4)_2HPO_4$ in 120 mL of D.I. water. Concentrated ammonium hydroxide (60 mL) was added followed by 90 ml of D.I. water. The mixture was stirred for 4 hours at room temperature.

A solution of 19.0 g of $Ca(NO_3)_2 \cdot 4H_2O$ in 468 mL of D.I. water was placed in a 3-neck 1L round bottom flask. The reaction setup included a mechanical stirrer, water cooled and low temperature (dry ice/isopropanol) condenser arrangement, and a rubber septum. The solution was heated to reflux with rapid stirring. The basic phosphate solution was added dropwise with a peristaltic pump over one hour. The heat was removed after the addition was complete and the reaction mixture stirred overnight at room temperature.

The hydroxyapatite slurry was treated with a solution of DETAPMDP (Ca/DETAPMDP mole ratio=1.1, pH of DETAPMDP 6.3) and stirred at room temperature for 2.5 hours. The phosphonate treated mixture was then reacted with $Mn(NO_3)_2 \cdot 6H_2O$ (Ca/Mn mole ratio=2.3) and stirred for an additional 3.5 hours.

The reaction mixture was divided among six 50 mL plastic centrifuge tubes and centrifuged at 2400 rpm for 15 minutes. The clear supernatant was discarded and the solid residue suspended in 50 mL of D.I. per tube and centrifuged at 2400 rpm. The milky suspension was decanted and set aside. The solid was washed/centrifuged twice more and the three washes combined. The milky suspension was re-centrifuged at 7000 rpm for 30 minutes. The clear supernatant was discarded and the solid pellet resuspended and centrifuged three additional times at 7000 rpm. The purified pellet was then suspended in 15 mL od D.I. water and analyzed. The following results were obtained.

size (average diameter, nm): 258
relaxivity ($mMolar^{-1}sec^{-1}$): 20.3
[Mn] (mole/liter): 0.0013
[Ca] (mole/liter): 1.921
% Mn (mole % relative to Ca): 0.07

In magnetic resonance imaging studies, a 30% enhancement of the liver was observed immediately post injection at a dose of 10 μmoles Mn/Kg animal body weight.

EXAMPLE 24

Replacement of Phosphate with Arsenate in Preparation of Hydroxyapatite and Substituted Hydroxyapatites The procedure according to Example 17 is used except that 0.1–100 mole % arsenate is substituted for the phosphate. For example, 9.51 grams $(NH_4)_2HPO_4$ and 1.49 grams $Na_2AsO_4$ were dissolved in 400 mL of D.I. water. To this was: added 100 mL of concentrated $NH_4OH$ with stirring. The rest of the procedure follows directly from Example 17.

EXAMPLE 25

Replacement of Phosphate with Vanadate in Preparation of Hydroxyapatite and Substituted Hydroxyapatites The procedure according to Example 17 is used except that 0.1–100 mole percent vanadate is substituted for the phosphate. For example, 9.51 grams $(NH_4)_2HPO_4$ and 1.40 grams $Na_3VO_4$ were dissolved in 400 mL of D.I. water. To this was added 100 mL of concentrated $NH_4OH$ with stirring. The rest of the procedure follows directly from Example 17.

EXAMPLE 26

Preparation at 100° C. of Mn-Doped Fluoroapatite Particles

Manganese fluoroapatite was prepared by the following general procedure. Into a 5-neck 1L round bottom flask equipped with a mechanical stirrer, water cooled reflux condenser, adapter for pH electrode, and two rubber septa for addition of reagents were placed 10.3 g of $Mn(OAC)_2 \cdot 4H_2O$ in 200 mL of D.I. water. The solution was degassed with heavy argon bubbling for 30 minutes. A solution of ammonium fluoride, $NH_4F$ (0.3 g) in 50 mL of D.I. water was prepared in a 125 mL erlenmeyer flask and degassed for 30 minutes with argon. Into a 250 mL erlenmeyer flask was placed 3.3 g of $(NH_4)_2HPO_4$ in 150 mL of D.I. water and degassed for 30 minutes before addition.

The manganese acetate solution was heated to reflux with rapid stirring (pH 6.6) and the $NH_4F$ and $(NH_4)_2HPO_4$ solutions were added dropwise simultaneously with a peristaltic pump over 35 minutes. The solid precipitated among immediate addition of reagents and was pale pink in color. The pH of the reaction mixture dropped to 4.7 by the end of the reaction. The heating was stopped when the addition was complete. The reaction mixture was stirred at room temperature overnight.

The apatite slurry was divided among four 50 mL plastic centrifuge tubes and centrifuged for 30 minutes at 2400 rpm. The clear supernatant was discarded, and the pale pink solid was resuspended and centrifuged for 30 minutes at 2400 rpm. The solid was washed and centrifuged twice more and the clear supernatants discarded. The purified solid pellet was suspended in 20 mL of D.I. water.

EXAMPLE 27

Preparation of Calcium Tungstate Diagnostic Composition

Commercially available calcium tungstate, $CaWO_4$, (Alfa) is milled to an average particle size of about 1 µm. The particles are coated with a conventional stabilizing agent., such as albumin. 20 gm of the calcium tungstate is suspended in 100 mL of a pharmaceutically acceptable injectable solution, to form a 20 weight percent diagnostic composition. This calcium tungstate diagnostic composition is administered in a typical dosage of about 24 mg W/Kg body weight.

EXAMPLE 28

Preparation of Manganese(II)-Containing Octacalcium Phosphate Coated with HEDP

Octacalcium phosphate doped with manganese(II) is prepared by dissolving 1.5 g calcium acetate and 0.12 g manganese acetate tetrahydrate in 100 mL of distilled, deionized deaerated (Ar bubbling, 1 hour) water. This solution is added over a 10 minute period to a solution of 1.15 g ammonium dihydrogen phosphate in 100 mL of distilled, deionized, deaerated (Ar bubbling, 1 hour) water that has been pH adjusted to 5 before addition is started. After addition is complete the reaction mixture is stirred for 10 minutes and treated with 0.55 g of a 60% HEDP solution in 10 mL of distilled, deionized water that has been pH adjusted to 5.5 and deaerated for 15 minutes with Ar. The reaction mixture is allowed to stir for 30 minutes and is worked up as in Example 17 (*Preparation at room temperature of Hydroxyapatite particles doped with Mn and treated with HEDP*) to harvest and purify the small (>5 micron) particles from this reaction.

From the foregoing, it will be appreciated that the present invention provides organ specific medical diagnostic imaging agents for use in MRI, X-ray, and ultrasound.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for enhancing medical diagnostic imaging of body organs and tissues which comprises:
    (a) administering to a patient, a diagnostically effective amount of calcium/oxyanion- containing particles which are treated to be echogenic, in a pharmaceutically acceptable carrier, said calcium/oxyanion-containing particles having a general formula:

$$Ca_nM_mX_rY_s$$

wherein M is a stoichiometric mixture of metal ions, X is a simple anion, Y is an oxyanion, tetrahedral oxyanion, protonated or unprotonated, carbonate, or mixtures thereof, m is from 0 to 10, n is from 1 to 10, s is $\geq 1$, and r is adjusted as needed to provide charge neutrality; and
    (b) imaging the organs and tissues using an ultrasound medical diagnostic imaging technique.

2. A method for enhancing medical diagnostic imaging as defined in claim 1 wherein Y is $PO_4^{3-}$, $AsO_4^{3-}$, $WO_4^{2-}$, $MoO_4^{2-}$, $VO_4^{3-}$, $SIO_4^{4-}$, or $GeO_4^{4-}$, and protonated forms.

3. A method for enhancing images as defined in claim 1, wherein the calcium/oxyanion-containing particles further comprise a coating agent to stabilize the calcium/oxyanion-containing particles.

4. A method for enhancing images as defined in claim 3, wherein the coating agent is selected from the group comprising di- and polyphosphonate-containing compounds, carboxylates and polycarboxylate-containing compounds, alcohols and polyalcohol-containing compounds, phosphates and polyphosphate-containing compounds, sulfates and sulfate-containing compounds, sulfonates and sulfonate-containing compounds, and biomolecules.

5. A method for enhancing images as defined in claim 3, wherein the coating agent is a di- and polyphosphonate-containing compound.

6. A method for enhancing images as defined in claim 3, wherein the coating agent is hydroxyethyldiphosphonate (HEDP).

7. A method for enhancing images as defined in claim 3, wherein the coating agent is a peptide, protein, antibody, or lipid biomolecule.

8. A method for enhancing images as defined in claim 3, wherein the coating agent comprises a reactive functional group.

9. A method for enhancing images as defined in claim 8, wherein the reactive functional group is an amine, active ester, alcohol, or carboxylate functional group.

10. A method for enhancing images as defined in claim 8, wherein the coating agent having a reactive functional group comprises:

$$\text{HO} - \overset{NH_2}{\underset{PO_3^{2-}}{\overset{|}{C}}} - PO_3^{2-}$$

11. A method for enhancing images as defined in claim 1, wherein the calcium/oxyanion-containing particles are administered parenterally.

12. A method for enhancing ultrasound images of body organs and tissues comprising:
    (a) administering to a patient, a diagnostically effective amount of echogenic calcium/oxyanion-containing particles, in a pharmaceutically acceptable carrier; and
    (b) imaging the organs and tissues using ultrasound techniques.

13. A method for enhancing ultrasound images of body organs and tissues as defined in claim 12, wherein the echogenic calcium/oxyanion-containing particles include gas-filled pores.

14. A method for enhancing ultrasound images of body organs and tissues as defined in claim 12, wherein the echogenic calcium/oxyanion-containing particles are prepared by mixing calcium/oxyanion-containing particles, having a carbonate salt incorporated therein, with a weak biocompatible acid, such that carbon dioxide is formed within pores of the calcium/oxyanion-containing particles.

15. A method for enhancing ultrasound images of body organs and tissues as defined in claim 12, wherein the echogenic calcium/oxyanion-containing particles are dense particles substantially without pores.

16. A diagnostic composition for enhancing medical diagnostic imaging suitable for parenteral administration to a patient which comprises:
    a diagnostically effective amount of calcium/oxyanion-containing particles which are treated to be echogenic, having a size in the range from about 5 nm to about 50

µm, said calcium/oxyanion-containing particles having a general formula:

$$Ca_nM_mX_rY_s$$

wherein M is a stoichiometric mixture of metal ions, X is a simple anion, Y is an oxyanion, tetrahedral oxyanion, protonated or unprotonated, carbonate, or mixtures thereof, m is from 0 to 10, n is from 1 to 10, s is $\geq 1$, and r is adjusted as needed to provide charge neutrality; and a pharmaceutically acceptable carrier.

17. A diagnostic composition for enhancing medical diagnostic imaging as defined in claim 16, wherein Y is $PO_4^{3-}$, $AsO_4^{3-}$, $WO_4^{2-}$, $MoO_4^{2-}$, $VO_4^{3-}$, $SiO_4^{4-}$, or $GeO_4^{4-}$, and protonated forms.

18. A diagnostic composition for enhancing ultrasound contrast suitable for parenteral administration to a patient which comprises:

a diagnostically effective amount of echogenic calcium/oxyanion-containing particles having a particle size in the range from about 5 nm to about 50 µm, said echogenic calcium/oxyanion-containing particles having a general formula:

$$Ca_nM_mX_rY_s$$

wherein M is a stoichiometric mixture of metal ions, X is a simple anion, Y is an oxyanion, tetrahedral oxyanion, unprotonated or unprotonated, carbonate, or mixtures thereof, m is from 0 to 10, n is from 1 to 10, s is $\geq 1$, and r is adjusted as needed to provide charge neutrality; and a pharmaceutically acceptable carrier.

19. A diagnostic composition as defined in claim 18, wherein the echogenic calcium/oxyanion-containing particles include gas-filled pores.

20. A diagnostic composition as defined in claim 18, wherein the echogenic calcium/oxyanion-containing particles are prepared by mixing calcium/oxyanion-containing particles, having a carbonate salt incorporated therein, with a weak biocompatible acid, such that carbon dioxide is formed within pores of the calcium/oxyanion-containing particles.

21. A diagnostic composition as defined in claim 18, wherein the echogenic calcium/oxyanion-containing particles are dense particles substantially without pores.

* * * * *